United States Patent
Maddern et al.

(10) Patent No.: US 6,432,429 B1
(45) Date of Patent: Aug. 13, 2002

(54) HAND CLEANSER

(75) Inventors: Peter Maddern, Flintshire (GB); Jesus Maria Zubillaga Yeregui, Vitoria (ES)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 09/463,812

(22) PCT Filed: Jul. 31, 1998

(86) PCT No.: PCT/GB98/02309
§ 371 (c)(1),
(2), (4) Date: May 8, 2000

(87) PCT Pub. No.: WO99/06021
PCT Pub. Date: Feb. 11, 1999

(30) Foreign Application Priority Data

Jul. 31, 1997 (GB) ................................................ 9716273

(51) Int. Cl.⁷ .......................... A01N 25/34; A61K 6/00; A61K 9/00; A61K 31/74; A61F 13/00
(52) U.S. Cl. ...................... 424/402; 424/401; 424/400; 424/443
(58) Field of Search ................................. 424/404, 402, 424/78.03, 401

(56) References Cited

U.S. PATENT DOCUMENTS

| | | |
|---|---|---|
| 3,933,674 A | 1/1976 | Farnsworth |
| RE29,649 E | 5/1978 | Farnsworth |
| 4,414,128 A | 11/1983 | Goffinet |
| 4,511,488 A | 4/1985 | Matta |
| 4,576,738 A | 3/1986 | Colodney et al. |
| 4,620,937 A | 11/1986 | Dellutri |
| 4,640,719 A | 2/1987 | Hayes et al. |
| 4,806,572 A * | 2/1989 | Kellett |
| 4,849,117 A | 7/1989 | Bronner et al. |
| 4,934,391 A | 6/1990 | Futch et al. |
| 5,011,620 A | 4/1991 | Dishart et al. |
| 5,062,988 A | 11/1991 | Dishart et al. |
| 5,084,200 A | 1/1992 | Dishart et al. |
| 5,130,056 A * | 7/1992 | Jakobson et al. |
| 5,167,853 A | 12/1992 | Stevens |
| 5,194,173 A | 3/1993 | Folkard et al. |
| 5,196,136 A | 3/1993 | Dishart et al. |
| 5,230,821 A | 7/1993 | Larson et al. |
| 5,277,836 A | 1/1994 | Peters |
| 5,360,580 A | 11/1994 | Dotolo et al. |
| 5,380,453 A | 1/1995 | Krawack |
| 5,415,788 A | 5/1995 | Vlasblom et al. |
| 5,425,893 A | 6/1995 | Stevens |
| 5,427,710 A | 6/1995 | Stevens |
| 5,441,666 A | 8/1995 | Dotolo |
| 5,443,749 A | 8/1995 | Dotolo |

(List continued on next page.)

FOREIGN PATENT DOCUMENTS

| | | | |
|---|---|---|---|
| EP | 0 498 545 | * | 8/1992 |
| EP | 0498545 A1 | | 12/1992 |
| EP | 615720 A1 | | 9/1994 |
| EP | WO 95/14753 | * | 6/1995 |
| EP | 761843 A2 | | 3/1997 |
| EP | 801130 A | | 10/1997 |
| WO | WO 9514753 | | 6/1995 |

OTHER PUBLICATIONS

PCT International Search Report; Appl. No. PCT/US99/27454.
PCT International Search Report; Appl. No. PCT/GB 98/02309.

Primary Examiner—Thurman K. Page
Assistant Examiner—Isis Ghali
(74) Attorney, Agent, or Firm—Dority & Manning, P.A.

(57) ABSTRACT

A hand cleansing article comprising a substrate capable of absorbing and retaining a fluid therein is provided. The substrate is impregnated with an aqueous hand cleanser formulation that includes (a) 1 to 10% by weight of a fatty acid ester or mixture of such esters; (b) 1 to 10% by weight of at least one emulsifying surfactant; and (c) from 75 to 99% by weight of water.

22 Claims, 2 Drawing Sheets

U.S. PATENT DOCUMENTS

| | | |
|---|---|---|
| 5,464,555 A | 11/1995 | Bayless |
| 5,494,611 A | 2/1996 | Dolan et al. |
| 5,587,357 A | 12/1996 | Rhinesmith |
| 5,604,193 A | 2/1997 | Vlasblom |
| 5,660,845 A * | 8/1997 | Trinh et al. .......... 424/418 |
| 5,683,971 A | 11/1997 | Rose et al. |
| 5,712,237 A | 1/1998 | Stevens |
| 5,728,662 A | 3/1998 | Vlasblom |
| 5,736,500 A | 4/1998 | Farnworth et al. |
| 5,783,200 A * | 7/1998 | Motley et al. .......... 424/401 |
| 5,837,274 A | 11/1998 | Shick et al. |
| 5,849,310 A | 12/1998 | Trinh et al. |
| 5,891,855 A | 4/1999 | Florkiewicz |
| 5,928,631 A * | 7/1999 | Lucas et al. |

\* cited by examiner

HAND CLEANSER

This application is a 371 of PCT/GB98/02309, filed Jul. 31, 1998.

The present invention relates to a cleanser, in particular a so-called "waterless" hand cleanser, and an abrasive hand cleansing article impregnated with such a cleanser.

Conventional hand cleansing formulations contain solvents and/or surfactants capable of solubilising or emulsifying soils present on the skin's surface. The cleansing power of such formulations is however limited, particularly when dealing with the removal of various heavy, ingrained soils such as may be encountered by those working in industry.

A number of hand cleansers currently being used are in the form of a gel which may contain both polar and non-polar ingredients blended together to achieve removal of a variety of soils from the surface of the skin. These often contain abrasive particles which scour the skin surface to aid in the removal of embedded soils. One disadvantage associated with such gels is the need to wash-off the gel residue or excess cleanser from the-skin following use. This means that the operation of hand cleansing takes longer and, in the case of industrial hand cleansing, this ultimately increases costs.

A further disadvantage associated with the use of gels is that, depending on the formulation, these have a tendency to remove the skin's natural protective lipids, particularly when the cleanser is used repeatedly, leaving the skin with no protection against dehydration once the gel residue has been rinsed off. This is a particular problem in areas of low humidity.

One solution to this problem has been presented in the form of so-called "waterless" formulations which do not require the addition of water or moisture to be activated. In particular these do not require rinsing of the hands with water after use.

A "waterless" formulation of this type is described in EP-A-615720 in which a d-limonene based formulation is used for cleansing the skin. However, such a formulation has a particularly high citrus fragrance, leaving the hands with an undesirable and long-lasting residual orange citrus odour following use. Furthermore, solvents such as d-limonene and the like, may remove some of the skin's natural fats and such a formulation may have only a limited tendency to re-fat or moisturise the skin after cleansing. Since d-limonene is extracted from orange peel, it is also relatively costly. Moreover, its availability is dependent upon crop yields and its price is thus subject to fluctuation.

As an alternative to d-limonene based formulations, a blend of paramenthadienes has recently been proposed for use as a cleansing agent (see WO-A-97/09033). However, as with d-limonene, there is frequent variation in the ingredient quality of such "natural" solvents due to crop variations. This can present difficulties in formulating a product of consistent quality.

There has also been growing concern recently over damage to the atmosphere due to the emission of volatile organic compounds from a wide variety of commercial products including industrial cleansing products, such as those containing the solvent d-limonene or isomers of d-limonene, e.g. paramenthadienes.

The use of particularly high concentrations of non-volatile vegetable oils and fatty acid esters has been proposed as a replacement for traditional volatile solvents for various cleaning purposes, particularly in the removal of printing ink and other oily contaminants from printing presses (see e.g. U.S. Pat. Nos. 5,104,567, 5,194,173, 5,380,453, 5,143,639 and SUBSPRINT Project—promoting the use of vegetable oil cleaning agents in the printing industry). EP-A-615720 also suggests that vegetable oils may be useful in solubilising greasy, oily soils from the skin.

Various oils, including vegetable oils and fatty acid esters, optionally in combination with other emollient oils such as mineral and/or silicone oils, have also been proposed for use in formulations for cleansing the face, e.g. to remove make-up compositions comprising natural and/or synthetic waxes (see e.g. U.S. Pat. Nos. 4,806,572 and 5,585,104).

However, we have now surprisingly found that oil-in-water emulsions comprising one or more fatty acid esters are effective as a "waterless" cleanser in the. removal of heavy duty contaminants, in particular ingrained soils, from the surface of the skin whilst at the same time potentially serving to effectively moisturise the skin. The present invention thus provides a hand cleanser formulation having a strong cleansing action, but which is also of mild and soothing benefit to the hands and, in particular, is non-irritating.

According to one aspect, the present invention thus provides an aqueous hand cleanser formulation comprising:
 (a) up to 25% by weight of a fatty acid ester or mixture of such esters;
 (b) at least one emulsifying surfactant; and
 (c) from 75 to 99% by weight of water.

Aqueous cleansing formulations in accordance with the invention have been found to be particularly effective in the removal of a variety of soils from the surface of the skin, in particular ingrained oily, greasy soils, and are thus envisaged to be of particular use to those working in industry.

The formulations in accordance with the invention can be used to cleanse the skin in the absence of any additional water during the cleansing process. The invention thus provides an alternative "waterless" hand cleanser which is not only effective in solubilising soils, but also which is believed to be effective in moisturising the skin without leaving any long-lasting residual odour on the skin surface.

Furthermore, the use of a fatty acid ester, or mixture of fatty acid esters, as the cleansing agent overcomes the problem of emission of volatile organic compounds associated with the use of conventional industrial cleansing agents. Thus, there are no vapour or unacceptable odour problems associated with the use of such agents in a hand cleansing formulation. Moreover, the cleansing formulations in accordance with the invention are biologically decomposable and thus present no disposal problems. They are also non-toxic.

Conveniently, the nature and amount of the surfactant present in the cleansing formulation is such that this is effective to stabilise the oil-in-water emulsion, i.e. this is capable-of emulsifying the fatty acid ester components and any other components present in the formulation which require emulsification. As a result, the cleansing formulation in accordance with the invention is preferably a substantially homogeneous emulsion.

Whilst not wishing to be bound by theoretical considerations, it is believed that maintaining the fatty acid ester in an oil-in-water emulsion enhances its cleansing potential since the emulsion has a larger volume than a "non-emulsified" mixture thereby allowing a greater solubilisation of oily, greasy deposits.

The fatty acid ester, or mixture of fatty acid esters, is an essential component of the cleansing formulation and may preferably constitute the principal cleansing agent present in the formulation. Preferably, the formulation in accordance with the invention is substantially free from any additional mineral or vegetable oil.

The formulation of the invention may contain further cleansing agents such as d-limonene and paramenthadienes e.g. in an amount of up to 10% by weight. However preferably, the formulations according to the invention are substantially free from any volatile organic solvents, such as paraffin hydrocarbons, alcohols etc. Particularly preferably, the formulation is substantially non-volatile.

As used herein, the term "fatty acid ester" is intended to cover any mono-, di- or tri-ester in which one or more ester moieties are derived from a fatty acid.

The aqueous cleansing emulsion suitable for use in the abrasive article according to the invention can contain a wide range of fatty acid esters.

In general, the fatty acid used to form the esters will have from 1 to 22 carbon atoms, preferably from 8 to 22, more preferably from 8 to 18, most preferably from 8 to 12. Particularly preferred fatty acids are those having an even number of carbon atoms. The fatty acids may be straight-chained, branched or cyclic. However, straight-chained fatty acids are in general preferred. The fatty acids may be saturated or unsaturated, preferably saturated.

Whilst the fatty acid component of the esters for use in the invention may be synthetically prepared, these are preferably derived from naturally occurring oils, such as animal fats and oils and vegetable oils. Most preferably, these are derived from vegetable oils, e.g. safflower oil, olive oil, coconut oil, cottonseed oil, menhaden oil, palm kernel oil, palm oil, peanut oil, soybean oil, rapeseed oil, linseed oil, rice palm oil, pine oil, sesame oil, wheat germ oil, primrose oil and sunflower seed oil. Accordingly, representative fatty acids include caprylic, caproic, capric, lauric, myristic, palmitic, stearic, behenic and erucic acid.

Other fatty acids suitable for use in the invention include heptanoic, oleic, linoleic and linolenic acids.

The alcohol used to form the fatty acid esters may be straight-chained, branched or cyclic. Preferred alcohols include short chain monohydric alcohols having from 1 to 12 carbon atoms, preferably from 2 to 10 carbon atoms, most preferably from 3 to 8 carbon atoms, particularly preferably 8 carbon atoms. Alternatively, the alcohol may be a diol or a polyol, such as glycerol, sorbitol, polyethylene glycol, polypropylene glycol or a polyglycol. Whilst the alcohol moiety may be saturated or unsaturated, saturated alcohols are in general preferred.

Particularly preferred alcohols for use in the formation-of the fatty acid esters include ethanol, propanol, butanol, pentanol, hexanol, heptanol and octanol and structural isomers thereof.

The fatty acid ester component may be present in amounts of from 1 to about 25%, preferably from about 1 to about 10%, and more preferably from about 3 to about 6% by weight of the aqueous cleansing formulation. In order to ensure that the cleanser formulation can be applied smoothly to the skin surface, the emulsion should not be too tacky such that the application of the formulation is uneven. In order to reduce excessive tackiness, it is preferable that the amount of fatty acid ester component in the emulsion be the minimum necessary to ensure effective cleaning and this amount will be readily determined by the person skilled in the art. Moreover, a low concentration of fatty acid ester will reduce the cost of the cleansing formulation.

Particularly preferred fatty acid esters for use in the invention include octyl stearate, octyl octanoate, octyl laurate, octyl cocoate and mixtures thereof. Octyl cocoate is commercially available as ESTOL 1540° from Unichema, Holland, or as CRODAMOL OC® from Croda, UK.

Surfactants suitable for use in the formulation of the invention may be non-ionic, ionic or amphoteric in nature, the only requirement being that the surfactant mixture serves to emulsify the fatty acid ester components and any other components present in the formulation which require emulsification. Any conventional surfactants or surfactant blends may be used.

Particularly preferably, the cleansing formulation comprises at least one non-ionic surfactant which serves as an emulsifier for the fatty acid ester component. A mixture of non-ionic surfactants may also be used. Preferred non-ionic surfactants include ethoxylated alcohols such as pareth, steareth, ceteth and ceteareth derived surfactants. The formulation of the present invention preferably comprises a total of from about 1% to about 25%, more preferably from about it to about 10%, most preferably from about 3% to about 6% by weight of a non-ionic surfactant or mixture of non-ionic surfactants.

In a preferred embodiment, the cleansing formulation comprises at least one non-ionic surfactant and at least one anionic surfactant, such as sodium laureth-11 carboxylate, sodium laureth sulphate and triethanolamine lauric sulphate. In this formulation, the anionic solvent conveniently comprises from about 0.01% to about 5%, preferably from about 0.5% to about 3% by weight of the formulation.

The compositions of the present invention comprise from about 75% to about 99% by weight water, more preferably from about 75% to about 95%, most preferably from about 80% to about 85%. The exact amount of water will depend on the form of the product and the desired moisture content but will be readily determined by the persons skilled in the art.

The formulations in accordance with the invention may further comprise one more additional organic solvents in an amount of from 0.01 to 10% by weight, preferably from 2 to 4% by weight, e.g. 3% by weight. Any additional organic solvent may serve to act as a further emulsifying agent effective to form a stable emulsion with the remaining components of the formulation. Such solvents may also be capable of solubilising polar contaminants such as paint and adhesives from the skin, thereby improving the cleansing efficiency of the formulation.

Suitable co-solvents include glycol ethers, such as PPG-2 methyl ether, PPG-1 n-propyl ether, PEG-2 n-butyl ether and PEG-2 dimethyl ether; short chain polyols; glycols, such as propylene and ethylene glycol; and lactates such as ethyl lactate, butyl lactate and ethylhexyl lactate. A particularly preferred co-solvent is propylene glycol.

In an alternative embodiment, the formulations in accordance with the invention may further comprise one or more additional cleansing agents such as d-limonene and paramenthadienes in a low concentration, for example, in an amount of from 0.01 to 10% by weight, preferably from 2 to 7% by weight, e.g. 3% by weight. The amount of d-limonene or paramenthadienes present in any formulation should be kept to a minimum in order to reduce the potential for volatile solvent emission into the atmosphere. Any further-cleansing agent will, of course, be emulsified by the surfactant mixture.

Additional components which may be present in the formulations of the invention include antioxidants such as butylated hydroxytoluene (BHT), butylated hydroxyanisole (BHA) or others such as citric acid, vitamin E and other tocopherol derivatives; fragrances such as orange citrus fragrance, lemon fragrance or floral fragrance; emollients, such as aloe barbadensis gel, sodium pyrrolidone carboxylate and allantoin; antimicrobial agents, such as methyldibromoglutaronitrile, conveniently carried on a carrier such as phenoxyethanol; or other standard antioxidants, emollients and preservatives.

Other examples of preservative agents for use in the formulation include $C_{1-5}$ parabens, e.g. methyl paraben and propyl paraben, phenoxyethanol, quaternary ammonium salts and 2-bromo-2-nitropropane-1,3-diol. The amount of any given antimicrobial agent or mixture thereof included in the formulation will depend on its potency and stability, but generally will lie in the range of from 0.1 to 1% by weight, e.g. 0.1 to 0.5% by weight.

The emulsion may also contain moisturisers to add to the moisturisation conferred by the fatty acid ester component. Emollients such as allantoin not only serve to moisturise the skin, but can also reduce the tackiness of the cleansing formulation, thereby aiding its application to the skin surface. Suitable amounts of emollients present in the formulation lie in the range of from 0.1 to 5% by weight, e.g. 0.3 to 0.5% by weight.

Suitable amounts of fragrance will generally lie in the range of from 0.1 to 1% by weight, e.g. 0.1 to 0.5% by weight. Suitable amounts of antioxidants lie in the range of from 0.01 to 0.2% by weight, e.g. from 0.01 to 0.03% by weight.

The formulations in accordance with the invention may be prepared in any conventional manner, e.g. by simple admixture of the components. Conveniently, as a first step the fatty acid ester component may be mixed with the surfactants and water, with any additional components subsequently being added with additional mixing.

Viewed from a further aspect the invention thus provides a process for the preparation of a cleanser formulation as hereinbefore described, said process comprising the step of admixing (a) up to 25% by weight of a fatty acid ester or mixture of such esters, (b) at least one emulsifying surfactant, and (c) from 75 to 99% by weight of water.

Fatty acid esters for use in the invention can be produced in a known manner by esterification of a suitable fatty acid or mixture of such acids with an alcohol. Fatty acids are readily available from the hydrolysis of vegetable oils. The resulting mixture of fatty acids and glycerol can be separated into its constituent components so that pure new fatty acid esters may be prepared.

Fatty acid esters for use in the invention may also be prepared in a known manner by interesterification of a suitable vegetable oil with an alcohol, optionally after preceding fractionation of the vegetable oil or by fractionation of the ester mixture to provide a mixture of fatty acid esters. In this case, the product is a fatty acid ester of the particular vegetable oil and has various fatty acid ester components reflecting the distribution of fatty acid components in the vegetable oil.

The formulations described herein are particularly effective in solubilising greasy, oily soils such as paint and grease from the skin. Moreover, such formulations are believed to provide moisturisation to the skin leaving the hands both clean and soft.

Viewed from a further aspect, the present invention thus provides the use of a cleanser formulation as hereinbefore defined as a hand cleanser.

Abrasive hand cleansing materials, more commonly known as wet-wipes, are capable of cleansing embedded soils from the skin without the need for rinsing. Such materials are predominantly made from airlaid cellulosic fibres which may be saturated with a suitable cleansing solution. The formulations defined above have been found to be particularly effective in removing heavy soils from the hands when incorporated into such abrasive hand cleansing materials.

According to a further aspect, the invention thus provides an abrasive hand cleansing article comprising a substrate having at least one abrasive surface and being capable of absorbing and retaining a fluid therein, said substrate being impregnated with an aqueous cleansing fluid comprising:

(a) up to 25% by weight of a fatty acid ester or mixture of such esters;

(b) at least one emulsifying surfactant; and (c) from 75 to 99% by weight of water.

Cleansing action is achieved by the cleansing fluid and abrasive action is achieved by the abrasive surface of the substrate, enabling the material to produce a mild scrubbing action on the skin and thus aid in removal of ingrained soils.

The substrate should be capable of absorbing and retaining a predetermined amount of fluid, such as the cleansing formulation associated therewith, sufficient to provide a substantially uniformly moist article. The absorbent nature of the substrate is conveniently achieved by means of a number of pores provided therein and which are capable of absorbing and retaining the aqueous cleansing formulation, e.g. by capillary action. The article should also be capable of readily releasing the aqueous formulation on contact with the skin.

In order to aid cleansing, the substrate comprises at least one abrasive surface. This enables the article to produce a mild scrubbing action on the skin and thus aid in the removal of ingrained soils, whilst not harming the skin by scratching. Thus, it is envisaged that the substrate will have two opposed surfaces, at least one of said surfaces having an abrasive material attached thereto or comprising an integral part thereof. It is, however, possible for both sides of the substrate to comprise abrasive surfaces. In the case where the substrate has one abrasive surface, the remaining side conveniently will have a smooth surface to aid in wiping.

The substrate may comprise a cloth-like towel consisting of a system of pores able to absorb and retain the aqueous cleansing fluid, yet capable of readily releasing the fluid onto the skin surface during use.

Conveniently, a plurality of abrasive towels containing the cleansing formulation are provided, either in a stack or any continuous perforated roll, the individual towels being readily separable along each line of perforation. The towels may be provided in a container in which an aqueous formulation is added to moisten the towels. Capillary action ensures that the cleansing fluid is evenly distributed throughout the stack or roll of towels, each towel containing an amount of cleanser sufficient to thoroughly cleanse the skin. Alternatively, the abrasive material is pre-soaked prior to or during the operation of converting it into stacks or rolls.

Non-woven thermoplastic wipes may be used as an abrasive substrate for the cleansing formulation. These can be made either by meltblowing or spunbonding, techniques which are both well known in the art, see for example U.S. Pat. Nos. 3,978,185 and 3,692,618.

The technique of meltblowing is preferred for producing the abrasive cleansing materials of the invention. This involves extruding a multiplicity of continuous thermoplastic polymer strands through a multiplicity of die orifices in a downward direction, the extruded polymer strand being broken up and dispersed into individual fibres by a forced air stream before being deposited onto a moving collecting surface. In addition, the fibres are substantially cooled by the air to prevent any significant bonding between individual fibres. Bonding of the web to obtain integrity and strength occurs as a separate downstream operation. Meltblown webs formed in this way are characterised by their softness, bulk, absorbency and low porosity with a degree of abrasion resistance.

Meltblown webs or sheets suitable for the wipes of the present invention are well known in the non-wovens industry. Typically, such materials are made of polypropylene, although other thermoplastic polymers such as polyethylene, poly(ethylene terephthalate), poly(butylene terephthalate), polymethylpentene, polycaprolactam and propylene ethylene co-polymer can also be used. Preferably, the polymers are present in an amount of from 15 to about 200 grams per square meter (gsm) of the material, more preferably about 35 gsm. The unique properties of meltblown webs enable retention of the liquid cleanser as well as ready transfer of the liquid to adjacent contacting meltblown webs through capillary action. At the same time, the web is able to readily transfer the liquid cleanser onto the skin during use and also serves to trap removed soils between the fibres following cleansing as well as to wick liquids away from the skin.

One or more meltblown layers may, if desired, be supported on a supporting web, which is preferably spunbonded, in order to increase the strength of the resulting materials. Such a material exhibits the strength of a spunbonded web whilst maintaining the abrasiveness of the meltblown layer.

Preferred abrasive substrates are dual texture macrofibre/microfibre meltblowns such as described in U.S. Pat. Nos. 4,775,582, 4,833,003, 4,853,281 and EP-A-256950. The terms "macrofibre" and "microfibre" are used herein to distinguish between webs having different pore size distributions. "Macrofibre" meltblown refers to webs having less than 65% of the pore volume attributable to pores having a size of from about 20 to about 60 microns. "Microfibre" meltblown refers to webs in which at least 65% of the pore volume is attributed to pores having a size of from about 20 to about 60 microns.

Dual texture macrofibre/microfibre polypropylene meltblowns comprising 28% by weight macrofibres and 72% by weight microfibres are particularly preferred.

The amount of liquid cleanser within each wipe or sheet may be from 100 to 500% by weight, suitably from about 150 to about 500% by weight, preferably from about 200 to about 450% by weight, more preferably from about 340 to about 400% by weight, and yet more preferably about 375% by weight. If the amount of cleanser is too low then the wipe will be too dry and will not adequately cleanser the skin. If the amount of cleanser is too high then the wipe will be too soggy and may tend to simply "push" the soily deposits over the skin. The cleanser fluid may also begin to pool in the container.

The publications referred to herein are incorporated by reference.

Figure 1:
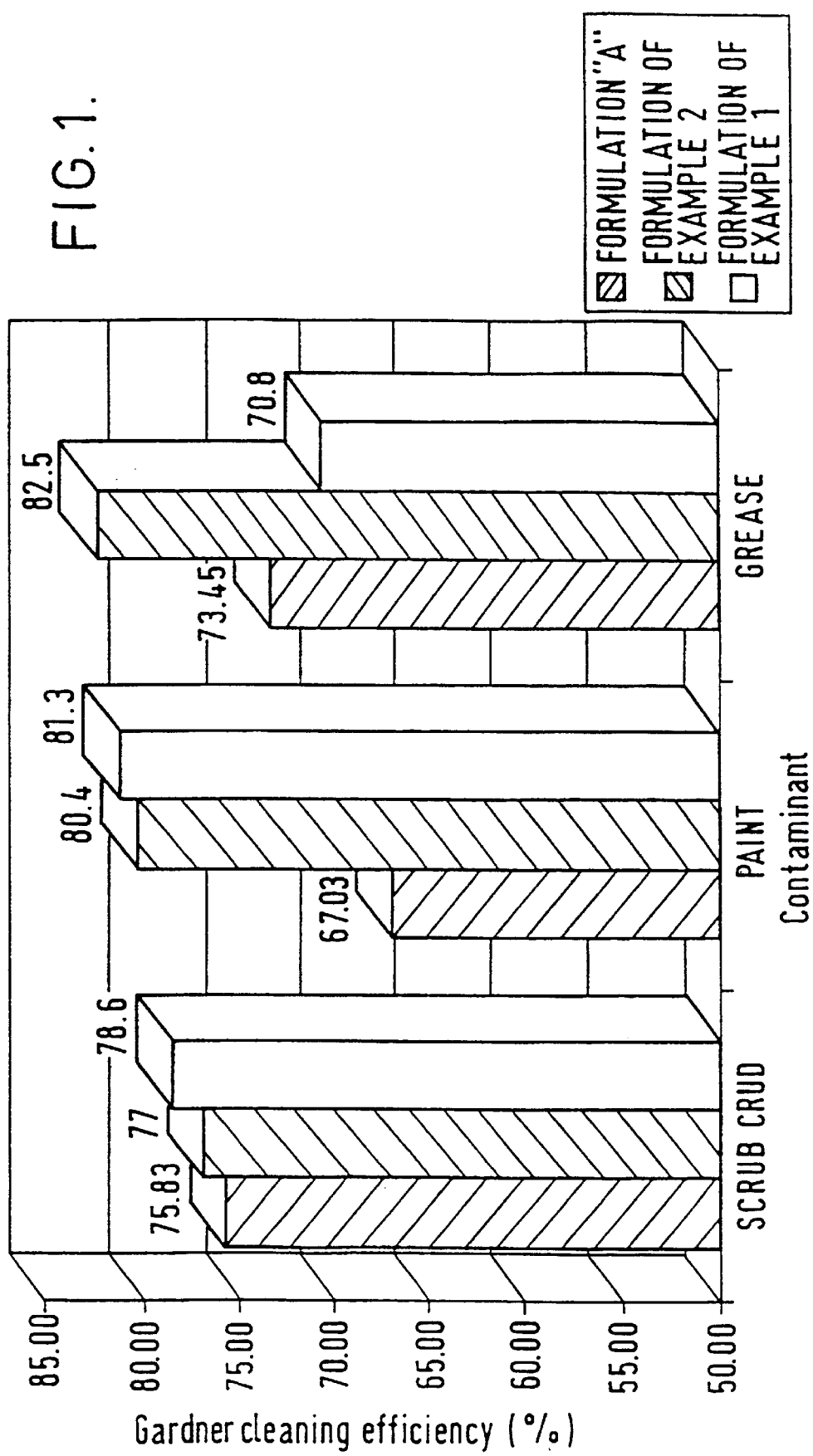
FIG. 1 is a graphical representation of the results obtained in Example 4.
Figure 2:
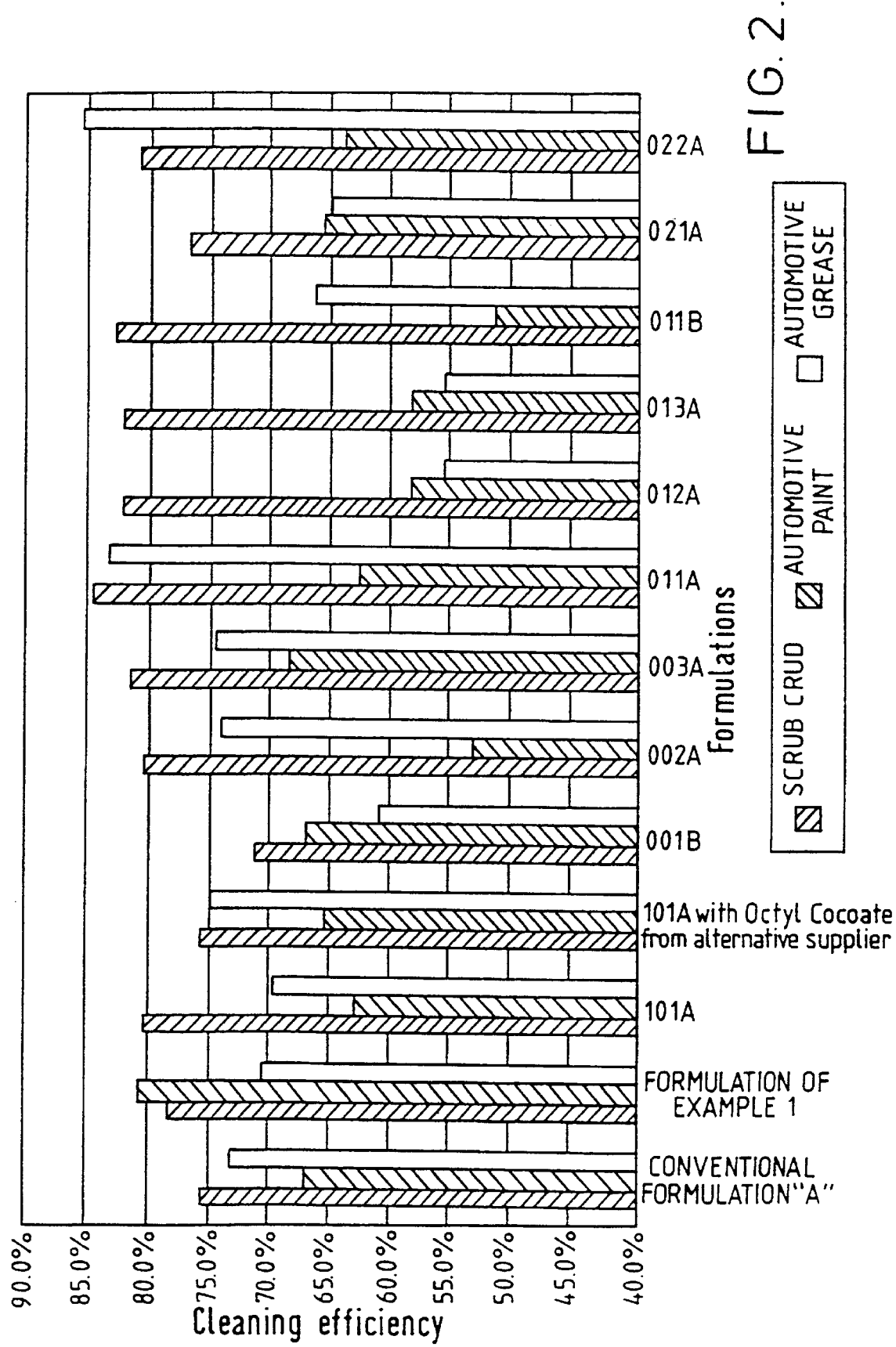
FIG. 2 is a graphical representation of the results obtained in Example 6.

The invention will now be illustrated by way of the wing non-limiting examples and with reference to attached FIGS. 1 and 2.

EXAMPLE 1

Hand Cleanser Formulation

|  | % by weight |
| --- | --- |
| Octyl Cocoate | 3.0 |
| Propylene glycol | 3.0 |
| $C_{11-15}$ Pareth-5 | 3.0 |
| Sodium Pyrrolidone Carboxylate (50% by weight aqueous solution) | 1.0 |
| Sodium Laureth-11 Carboxylate (22% by weight aqueous solution) | 2.5 |
| Methylparaben | 0.1 |
| Propylparaben | 0.1 |
| Quaternium-15 | 0.2 |
| Water | up to 100 |

The above ingredients were mixed in the given proportions to produce a liquid cleanser.

Use of the cleanser was found to be effective in removing SCRUB CRUD®, paint and grease in subjective hand wiping tests. Any excess cleanser did not require water for removal from the hands but was simply wiped off with a towel or cloth.

The cleanser left the hands clean and soft, with minimal residual odour.

EXAMPLE 2

Hand Cleanser Formulation

|  | % by weight |
| --- | --- |
| PPG-1n-Propyl Ether | 4.0 |
| D-Limonene (Dipentene) | 7.0 |
| Alcohol ethoxylate (OE 7) | 4.0 |
| PEG-200 Hydrogenated Glyceryl Palmitate and PEG-7 Glyceryl Cocoate (blend) | 3.0 |
| Methyl Paraben | 0.2 |
| Propyl Paraben | 0.1 |
| Quaternium 15 | 0.1 |
| Tocopheryl acetate | 0.1 |
| B.H.A. | 0.02 |
| Water | up to 100 |

The above ingredients were mixed in the given proportions to produce a liquid cleanser.

Use of the cleanser was found to be effective in removing SCRUB CRUD®, paint and grease in subjective hand wiping tests. Any excess cleanser did not require water for removal from the hands but was simply wiped off with a towel or cloth.

The cleanser left the hands clean and soft.

EXAMPLE 3

Wet Wipe Containing Cleanser Formulation

Dual texture macrofibre/microfibre polypropylene meltblowns (1.02 osy) comprising 28% by weight macrofibres and 72% by weight microfibres were produced in accordance with EP-A-0573277. These were then impregnated with either the liquid cleanser of Example 1 or 2 in a ratio of 3.5 g of the cleanser formulation per g of the meltblown.

When used in hand wiping tests, there was no need to use any cloth for removal of excess cleanser. Use of the wet wipes was found to be particularly effective in removing SCRUB CRUD®, paint and grease in subjective hand wiping tests. The wet wipes left the hands clean and soft, with minimal residual odour.

EXAMPLE 4

Cleaning Efficiency of Wet Wipe

The wet wipes of Example 3 were tested for cleaning efficiency using a Gardner washability apparatus. Various soils were applied to a square 50 mm² section of a textured vinyl substrate. The soiled panels were then mechanically cleaned with the abrasive side of the wet wipes wrapped around a block weighing 469 g, this weight being designed to simulate the effect of pressure applied when cleaning the hands. The panels were cleaned for a fixed number of cycles depending of the particular soil under test.

The cleaned soiled areas of the vinyl substrate panels were measured using a colourmeter and compared to the initial reflectance (whiteness) of the vinyl substrate prior to soiling. The final relectance after cleaning was taken to be the average of several readings. The cleaning efficiency is the ratio of final reflectance compared to initial reflectance. Typically, the test was repeated five times to obtain an average result.

The cleaning efficiency tests were repeated using a conventional liquid cleanser incorporated in an identical meltblown, the cleanser having the following composition:

| Conventional formulation A: | |
|---|---|
| | % by weight |
| Blend of paramenthadienes (TABS DS Terpene mixture) | 7.00 |
| PEG-40 Hydrogenated Castor Oil | 6.00 |
| PPG-1-PEG-9 Lauryl Glycol Ether | 6.00 |

| -continued | |
|---|---|
| Conventional formulation A: | |
| | % by weight |
| PPG-2 Methyl Ether | 4.00 |
| Parfum (Orange citrus fragrance) | 1.20 |
| BHT | 0.462 |
| Phenoxyethanol | 0.16 |
| Methyldibromo Glutaronitrile | 0.04 |
| Aloe Barbadensis Gel | 0.01 |
| Aqua (water) | 75.128 |

The results of the cleaning efficiency tests are given in attached FIG. 1.

EXAMPLE 5

Hand Cleanser Formulations

Cleanser formulations were prepared by admixing in the required amounts the ingredients shown below in Table 1.

Use of the cleanser formulations was found to be particularly effective in removing SCRUB CRUD®, paint and grease in subjective hand wiping tests. Any excess cleanser did not require water for removal from the hands but was simply wiped off with a towel or cloth.

In each case, the cleanser formulation left the hands clean and soft, with minimal residual odour.

| Ingredients | 101-A | 001-B | 002-A | 003-A | 011-A | 012-A | 013-A | 011-B | 021-A | 022-A |
|---|---|---|---|---|---|---|---|---|---|---|
| Octyl Cocoate | 3.0 | 3.0 | — | — | 6.0 | — | — | 6.0 | 9.0 | — |
| Octyl Octanoate | — | — | — | 3.0 | — | — | 6.0 | 3.0 | — | — |
| Octyl Laurate | — | — | 3.0 | — | — | 6.0 | — | — | — | 9.0 |
| Propylene Glycol | 3.0 | — | 3.0 | 3.0 | 3.0 | 3.0 | 3.0 | — | 3.0 | 3.0 |
| $C_{11-15}$ Pareth-5 | 3.0 | 3.0 | 3.0 | 3.0 | 6.0 | 6.0 | 6.0 | 9.0 | 9.0 | 9.0 |
| Sodium Laureth-11 Carboxylate (22%) | 3.0 | 3.0 | 3.0 | 3.0 | 3.0 | 3.0 | 3.0 | 3.0 | 3.0 | 3.0 |
| Sodium Pyrrolidone Carboxylate (50%) | 0.5 | 0.5 | 0.5 | 0.5 | 0.5 | 0.5 | 0.5 | 0.5 | 0.5 | 0.5 |
| Allantoin | 0.2 | 0.2 | 0.2 | 0.2 | 0.2 | 0.2 | 0.2 | 0.2 | 0.2 | 0.2 |
| Phenoxyethanol Methylparaben Propylparaben 2-bromo-2-nitropropane-1,3-diol | 0.5 | 0.5 | 0.5 | 0.5 | 0.5 | 0.5 | 0.5 | 0.5 | 0.5 | 0.5 |
| Fragrance | — | 0.1 | 0.1 | 0.1 | — | — | — | — | — | — |
| Water | 86.8 | 89.7 | 86.7 | 86.7 | 80.8 | 80.8 | 80.8 | 77.8 | 74.8 | 74.8 |

EXAMPLE 6

Cleaning Efficacy of Wet Wipes Containing Cleanser Formulation

Dual texture meltblowns prepared as described in Example 3 were impregnated in a 3.5:1 ratio with the cleanser formulations of Example 5. These were then tested for cleaning efficacy according to the method described in Example 4. The results of the tests appear in attached FIG. 2.

What is claimed is:
1. A hand cleansing article comprising a nonwoven fibrous substrate that is capable of absorbing and retaining a fluid therein, said substrate being impregnated with an aqueous hand cleanser formulation comprising:
   a) 1 to 10% by weight of a fatty acid ester or mixture of such esters;
   b) 1 to 10% by weight of at least one emulsifying surfactant; and
   c) from 75 to 99% by weight of water;

wherein the fatty acid ester has a fatty acid component and an alcohol component, said fatty acid component comprising 8 to 22 carbon atoms and said alcohol component comprising 8 to 12 carbon atoms, and wherein said formulation is substantially free of mineral or vegetable oil.

2. A hand cleansing article as described in claim 1, wherein the fatty acid component of said fatty acid ester comprises 8 to 12 carbon atoms.

3. A hand cleansing article as described in claim 1, wherein the fatty acid component of said fatty acid ester is derived from vegetable oil.

4. A hand cleansing article as described in claim 3, wherein said vegetable oil is safflower oil, olive oil, coconut oil, cottonseed oil, menhaden oil, palm kernel oil, palm oil, peanut oil, soybean oil, rapeseed oil, linseed oil, rice palm oil, pine oil, sesame oil, wheat germ oil, primrose oil or sunflower seed oil.

5. A hand cleansing article as described in claim 1, wherein said fatty acid ester component comprises octyl stearate, octyl octanoate, octyl laurate, octyl cocoate or mixtures thereof.

6. A hand cleansing article as described in claim 1, wherein said fatty acid ester component comprises 3 to 6% by weight of the aqueous cleansing formulation.

7. An abrasive hand cleansing article comprising a nonwoven fibrous substrate having at least one abrasive surface and being capable of absorbing and retaining a fluid therein, said substrate being impregnated with an aqueous hand cleanser formulation comprising:

a) 1 to 10% by weight of a fatty acid ester or mixture of such esters;
  b) 1 to 10% by weight of at least one emulsifying surfactant; and
  c) from 75 to 99% by weight of water;
  wherein said fatty acid ester has a fatty acid component and an alcohol component, said fatty acid component comprising 8 to 12 carbon atoms and said alcohol component comprising a monohydric alcohol having 8 to 12 carbon atoms; and
  wherein said formulation is substantially free of mineral or vegetable oil.

8. An article as claimed in claim 7 wherein one side of the article is abrasive and the other side is smooth.

9. A hand cleansing article as defined in claim 1, wherein the fatty acid component of said fatty acid ester comprises an even number of carbon atoms.

10. A hand cleansing article as defined in claim 1, wherein the fatty acid component of said fatty acid ester comprises straight carbon chains.

11. A hand cleansing article as defined in claim 1, wherein the alcohol component of said fatty acid ester comprises a monohydric alcohol having 8 carbon atoms.

12. A hand cleansing article as defined in claim 1, wherein the alcohol component of said fatty acid ester comprises a saturated straight chain alcohol.

13. A hand cleansing article as defined in claim 1, wherein said emulsifying surfactant comprises at least one non-ionic surfactant or a mixture of at least one non-ionic surfactant and at least one anionic surfactant.

14. A hand cleansing article as defined in claim 13, wherein said non-ionic surfactant comprises pareth, steareth, ceteth, or ceteareth derived surfactants.

15. A hand cleansing article as defined in claim 13, wherein said non-ionic surfactant comprises 3% to 6% by weight of the aqueous cleansing formulation.

16. A hand cleansing article as defined in claim 13, wherein said anionic surfactant comprises sodium laureth-11 carboxylate, sodium laureth sulphate or triethanolamine lauric sulphate.

17. A hand cleansing article as defined in claim 13, wherein said anionic surfactant comprises 0.5% to 3% by weight of the aqueous cleanser formulation.

18. A hand cleansing article as defined in claim 1, wherein said formulation comprises 80 to 85% by weight water.

19. A hand cleansing article as defined in claim 1, wherein said formulation further comprises an organic solvent in an amount of 0.01 to 10% by weight.

20. A hand cleansing article as defined in claim 19, wherein said organic solvent comprises a glycol ester, a short chain polyol, or a lactate.

21. A hand cleansing article as defined in claim 19, wherein said organic solvent comprises a propylene glycol.

22. A hand cleansing article as defined in claim 1, wherein said formulation further comprises d-limonene or paramenthadiene in an amount from 0.01 to 10% by weight.

* * * * *